United States Patent [19]
Furuhashi et al.

[11] Patent Number: 5,518,603
[45] Date of Patent: May 21, 1996

[54] OXYGEN SENSOR AND A PROCESS FOR PRODUCTION THEREOF

[75] Inventors: Hiroshi Furuhashi, Nagoya; Syozo Tanida, Anjo; Toshitaka Saito, Toyohashi, all of Japan

[73] Assignee: Nippondenso Co., Ltd., Kariya, Japan

[21] Appl. No.: 171,961

[22] Filed: Dec. 23, 1993

Related U.S. Application Data

[63] Continuation of Ser. No. 772,912, Oct. 10, 1991, abandoned.

[30] Foreign Application Priority Data

Oct. 11, 1990 [JP] Japan ................................ 2-274295

[51] Int. Cl.$^6$ ................................................ G01N 27/407
[52] U.S. Cl. ........................ 204/429; 204/426; 264/56; 264/60; 264/61
[58] Field of Search ................... 204/153.18, 421–429; 264/56, 60, 61

[56] References Cited

U.S. PATENT DOCUMENTS

| | | | |
|---|---|---|---|
| 3,645,875 | 2/1972 | Record et al. | 204/429 |
| 4,582,657 | 4/1986 | Shibata et al. | 204/429 |
| 4,915,814 | 4/1990 | Harada et al. | 204/429 |

FOREIGN PATENT DOCUMENTS

| | | |
|---|---|---|
| 0168938 | 1/1986 | European Pat. Off. . |
| 56-93039 | 7/1981 | Japan . |
| 59-182270 | 10/1984 | Japan . |
| 60-259952 | 12/1985 | Japan . |
| 62-7667 | 1/1987 | Japan . |
| 62-207761 | 9/1987 | Japan . |

OTHER PUBLICATIONS

Hackh's Chemical Dictionary, 4th ed., (1969) month unavailable, p. 627.

*Primary Examiner*—T. Tung
*Attorney, Agent, or Firm*—Cushman, Darby & Cushman

[57] ABSTRACT

An oxygen concentration detecting device has a solid electrolyte made of a partially stabilized zirconia on one face of which is formed a measuring electrode exposed to a gas to be measured and on the other face of which a standard electrode exposed to a standard gas. An oxygen concentration detecting device provided with a protecting layer covers the measuring electrode formed on the oxygen concentration detecting device on the face exposed to the gas to be measured, the protecting layer being made of a partially stabilized sintered material of a partially stabilized zirconia material having a specific surface area of not less than 3 m$^2$/g and not more than 6.4 m$^2$/g to which a divalent or trivalent metal oxide, such as yttria, is added.

13 Claims, 2 Drawing Sheets

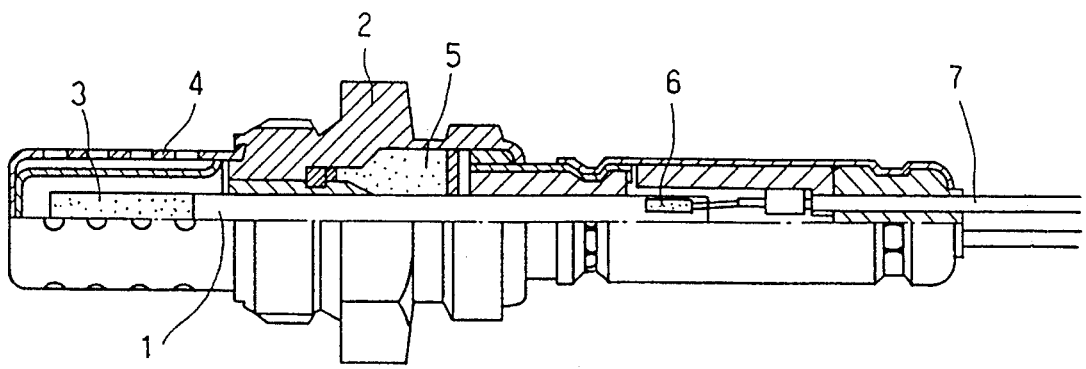
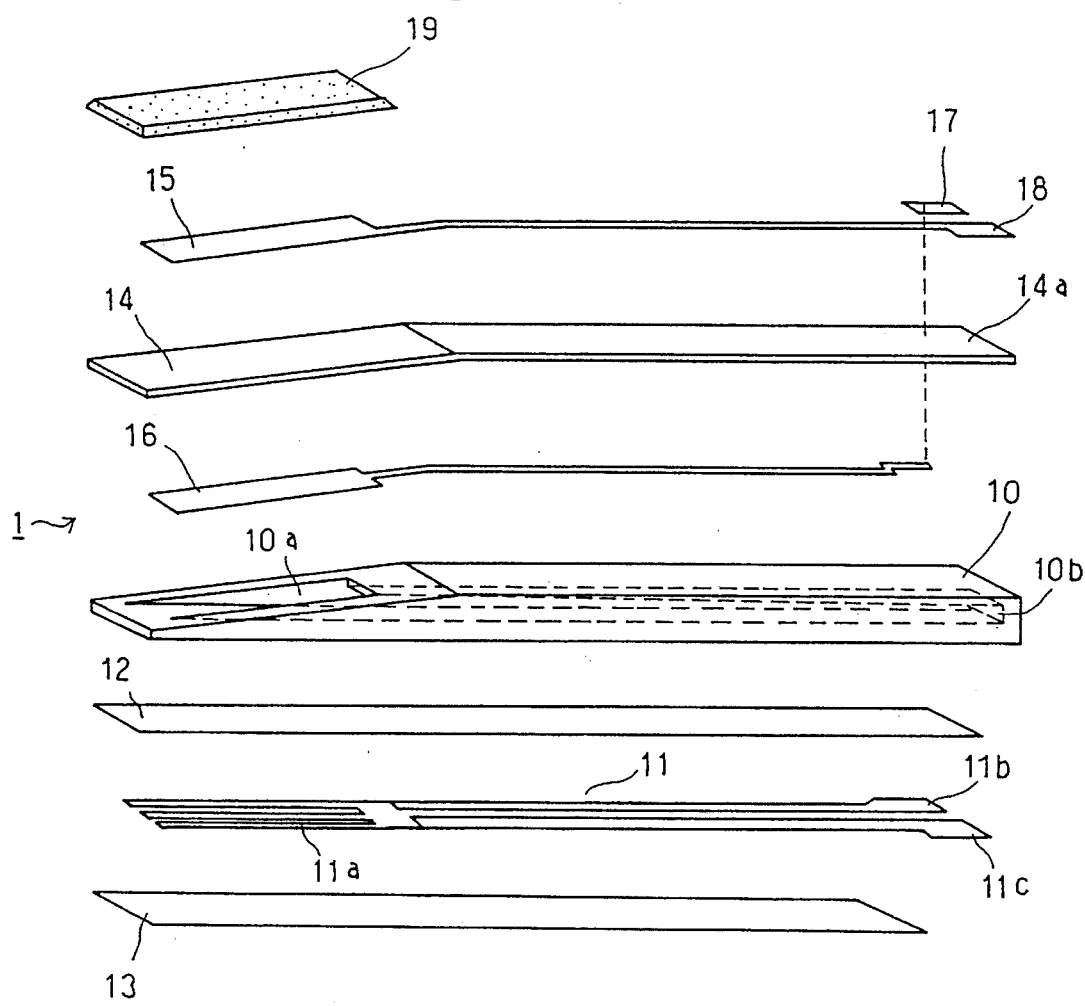

OXYGEN SENSOR AND A PROCESS FOR PRODUCTION THEREOF

This is a continuation of application No. 07/77,912, filed on Oct. 10, 1991, which was abandoned upon the filing hereof.

BACKGROUND OF THE INVENTION

1. Field of the Invention

The present invention relates to an oxygen concentration detecting device, and in particular, to an insulating layer formed on the measuring electrode of the oxygen concentration detecting device.

2. Description of the Prior Art

An oxygen concentration detecting device comprises a solid electrolyte, a pair of electrodes sandwiching the solid electrolyte and an insulating layer covering one of said electrodes contacting exhaust gas.

In order to obtain an oxygen concentration detecting device, it has conventionally been carried out to simultaneously sinter after stacking a solid electrolyte, electrodes and an insulating layer on each other because such a production method is simple and a high adhesive force can be obtained easily.

However, in the conventional method an insulating layer made of a partially stabilized zirconia containing monoclinic and tetragonal phases, which is the same material as the solid electrolyte, is provided in order to obtain a high adhesive force, however in this method, since the insulating layer is a rough and porous layer having a lower density than the solid electrolyte, micro cracks are generated in the insulating layer when a phase transition between monoclinic phase and tetragonal phase occurs due to the volume change at the phase transition, which is characteristic to zirconia, so that there has been a problem in that the mechanical strength of the insulating layer lowers remarkably, to the extent that it exfoliates at several tenth to several hundredth cycle in a cold-hot durability test wherein the maximum temperature is 1000° C.

Because of this, as disclosed in Japanese Patent Application Laid Open No. 259952/1985, it was proposed to use not the same material as the solid electrolyte but a completely stabilized zirconia composed only of cubic phase for the insulating layer.

However, when the insulating layer material of Japanese Patent Application Laid Open No. 259952/1985 is applied, since the thermal expansion coefficient of the completely stabilized zirconia as an insulating layer material is not less than $10 \times 10^{-6}/°$ C. while that of a monoclinic phase-containing partially stabilized zirconia as a solid electrolyte is generally $7-9 \times 10^{-6}/°$ C., it has been found that exfoliation occurs due to the difference in thermal expansion coefficient, which gives rise to a problem in durability.

The present invention has been achieved in view of the above problem, and an object of the invention is to provide an oxygen concentration detecting device which is excellent in durability and mechanical strength. Another object of the invention is to provide a method for producing an oxygen concentration detecting device which is excellent in durability and can be produced easily.

SUMMARY OF THE INVENTION

Accordingly, as a result of intensive studies carried out by the inventors, they have found that by varying the specific surface area of zirconia as an insulating layer material, although the insulating layer is partially stabilized, the volume change thereof due to phase transition can be avoided, and a thermal expansion coefficient which is almost the same as that of a solid electrolyte is obtained.

This is because even if the insulating layer is formed by using a partially stabilized zirconia composed of monoclinic phase and cubic phase, by varying the specific surface area of the zirconia, the temperature of phase transition from monoclinic phase to tetragonal phase can be elevated, and the amount of transition within the using temperature range of from room temperature to 1000° C., can be decreased, so that the thermal expansion coefficient of the insulating layer can be set to a desired value and the occurrence of cracks due to the volume change can be prevented.

From the above finding, a first invention of the present aspect obtained an oxygen concentration detecting device, comprising a solid electrolyte made of a partially stabilized zirconia with one face of which exposed to a gas to be measured and the other face of which exposed to a standard gas, a measuring electrode formed on one of the faces of the solid electrolyte and exposed to the gas to be measured, a standard electrode formed on the other face of the solid electrolyte, exposed to the standard gas and forming a pair together with the measuring electrode through the solid electrolyte, an insulating layer which is a porous partially stabilized sintered body and which covers the measuring electrode on the face exposed to the gas to be measured, main starting materials of the porous partially stabilized sintered body being zirconia and a metal oxide, the zirconia having a specific surface area of not less than 3 m$^2$/g and not more than 6.4 m$^2$/g before sintering, and the metal oxide being penetrated into spaces between zirconia crystals to elevate a temperature of phase transition between monoclinic phase and tetragonal phase of the zirconia to cause the thermal expansion coefficient to approximate that of the solid electrolyte.

As a second aspect, the present invention provides a method for producing an oxygen concentration detecting device, includes forming a measuring electrode on one face of a solid electrolyte made of a partially stabilized zirconia for exposure to a gas to be measured, forming a standard electrode on the other face of the solid electrolyte, forming zirconia and a metal oxide as main starting materials on the measuring electrode, the zirconia having a specific surface area of not less than 3 m$^2$/g and not more than 6.4 m$^2$/g, and sintering the solid electrolyte, measuring electrode, standard electrode and main starting materials to form a porous partially stabilized insulating layer including the zirconia and metal oxide, the metal oxide penetrating into spaces between zirconia crystals to elevate the temperature of phase transition between monoclinic phase and tetragonal phase of said zirconia to cause the thermal expansion coefficient of the insulating layer to approximate that of the solid electrolyte.

By employing the first aspect of this invention, since the specific surface area of zirconia as a main starting material of the insulating layer was made to be not less than 3 m$^2$/g and not more than 6.4 m$^2$/g, the penetration of the metal oxide into the space between zirconia crystals was controlled to a proper amount, therefore while the insulating layer was made of a partially stabilized zirconia composed of a monoclinic phase and a cubic phase, due to the penetration of the metal oxide into the space between zirconia crystals, the temperature of phase transition between monoclinic phase and tetragonal phase could be elevated by changing the material property of the zirconia. Because of this, the occurrence of micro cracks generated by this phase transition could be reduced to a large extent, and the thermal expansion coefficient at 1000° C. could be made to $7-9\times10^{-6}$/°C. to obtain almost the same thermal expansion coefficient as the solid electrolyte, so that the cold-hot durability could be improved.

By employing the second aspect of this invention, since the specific surface area of zirconia as a main starting material of the insulating layer was made to be not less than 3 m²/g and not more than 6.4 m²/g, even when the solid electrolyte, measuring electrode, standard electrode and insulating layer were sintered, the difference in thermal expansion coefficient between the solid electrolyte and the insulating layer could be made negligibly small, so that an oxygen concentration detecting device which is excellent in durability and can be produced easily could be provided.

By employing the present invention, not only an oxygen concentration detecting device which is excellent in durability and mechanical strength was obtained, but also a method for producing an oxygen concentration detecting device which is excellent in durability and can be produced easily could be provided.

BRIEF DESCRIPTION OF THE DRAWINGS

FIG. 1 is a cross sectional view of an oxygen concentration detecting device to be employed as an example of the present invention.

FIG. 2 is a developed view of the oxygen concentration detecting device of the invention.

DETAILED DESCRIPTION OF THE PREFERRED EMBODIMENTS

Figure 3:
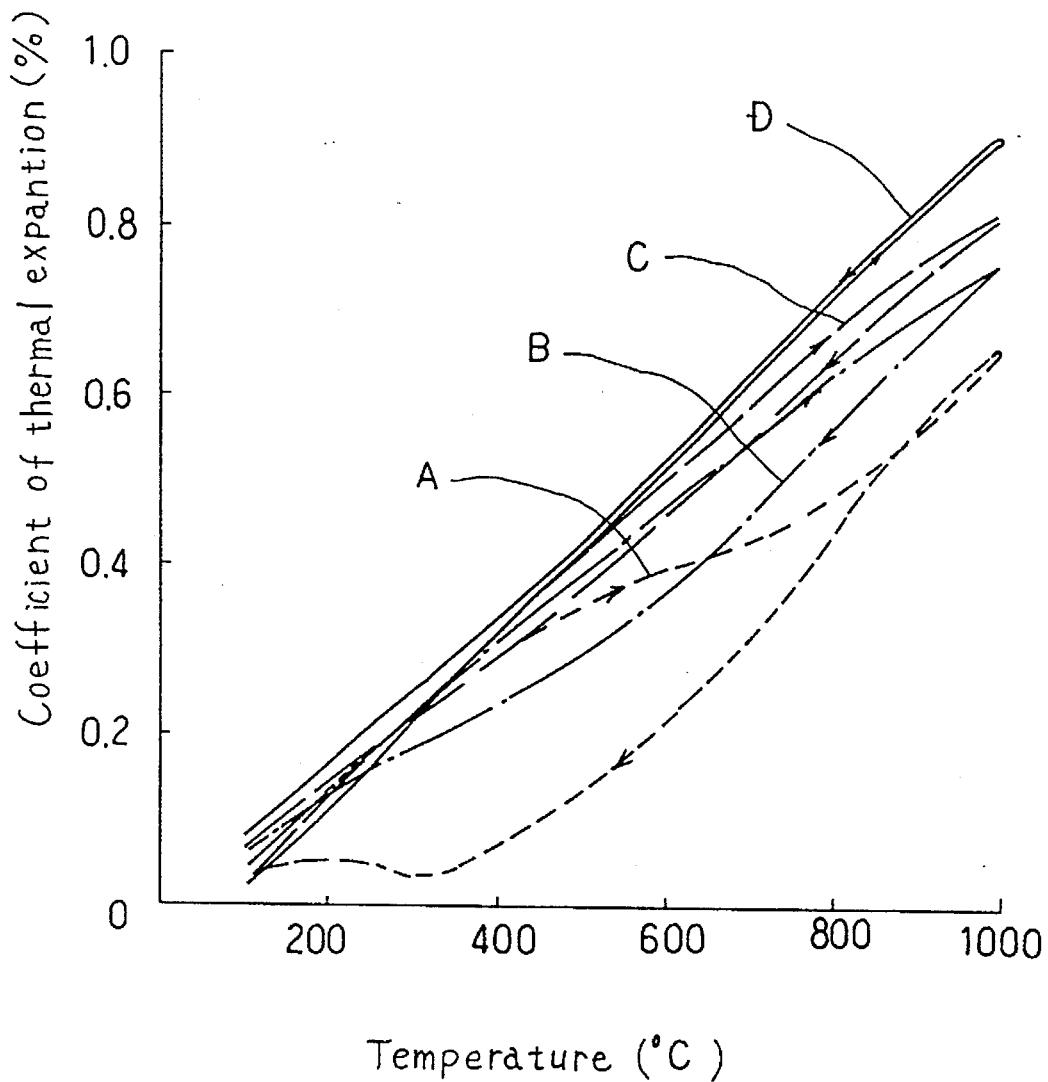
FIG. 3 is a characteristic drawing showing the thermal expansion cooling curves of the protecting layer at various specific surface areas against temperature.

FIG. 1 shows a cross sectional view of a part of an oxygen concentration detecting device to be applied to the present example.

In FIG. 1, 1 is an oxygen concentration detecting device, 2 is a housing provided with a protecting cover 4 for preventing the detecting part 3 of the oxygen concentration detecting device 1 from being directly exposed to an exhaust gas. In the housing 2, the oxygen concentration detecting device 1 is attached and fixed to the housing 4 through a powder 5 such as talc by means of thermal caulking or the like.

A lead wire 7 of which one end is connected by means of soldering or the like to a terminal electrode part 6 of the oxygen concentration detecting device 1 is guided to the exterior of the oxygen concentration detecting device main body.

FIG. 2 is a developed view showing an example of the oxygen concentration detecting device 1 of this example.

In FIG. 2, 10 is a square pipe-like supporting body having a rectangular-shaped cross section, made of an alumina ceramic and having a through-hole opening to both ends thereof. The open end surface 10a of the through-hole of this supporting body 10 on the side which is to be exposed to exhaust gas forms a sloped surface continuing from one of the side surfaces, and when viewed from the side, the end part thereof has a wedge shape. On the other end of the through-hole, an air inlet 10b is provided for the introduction of air.

Heating body 11 is mainly composed of platinum metal, which is stacked with an insulating layer 12 made of alumina or the like interposed in such a manner that it completely covers the surface opposing the sloped surface of the supporting body 10, that is, in such a manner that the heating part 11a of the heating body 11 completely covers the opening part 10a when viewed as a projection drawing. Moreover, to the heating body 11, another insulating layer 13 made of the same material as the insulating layer 12 is stacked on the part other than terminal electrodes 11b and 11c.

Solid electrolyte 14 is made of a partially stabilized zirconia prepared by sintering zirconia to which, for example, yttria, which is a metal oxide, is added. One face of the solid electrolyte is exposed through a measuring electrode 15 to a gas to be measured, and the other face is exposed through a standard electrode 16 to a standard gas. Moreover, this solid electrolyte 14 is stacked in such a manner that it seals the open end part 10a of the through-hole of the supporting body 10 through the standard electrode 16.

Furthermore, the standard electrode 16 is connected to a standard electrode terminal 17 through a through-hole 14a formed in the end part of the solid electrolyte 14, and the measuring electrode 15 is connected to a measuring electrode terminal 18.

Insulating layer 19 is a protecting layer which prevents the measuring electrode 15 from being directly exposed to the gas to be measured. This protecting layer 19 is made of a partially stabilized zirconia prepared by sintering a ceramic material having a specific surface area of 4.1 m²/g and a particle size of 0.93 μmm to which yttria, as a metal oxide, is added at an amount of 5 mol %.

Next, the production method of the oxygen concentration detecting device of the invention will be described.

The shape of a supporting body 10 is determined by injection molding or the like. On the bottom side surface of this supporting body 10, insulating layers 12 and 13, and a heating body 11 are formed by a printing method.

A solid electrolyte 14 is stacked on the supporting body 10 after being formed with electrodes 15 and 16 on both sides of the solid electrolyte 14 and a protecting layer 19, by a printing method.

Thereafter, by a simultaneous sintering, an oxygen concentration detecting device of the invention can be obtained.

Herein, yttria is added to protecting layer 19 at an amount 5 mol % in this example. However, it is preferred that yttria is added at an amount of 5–7 mol %. The reason for this is that if the amount of yttria is less than 5 mol %, the amount of penetration of yttria into the space between zirconia crystals is too small, so that there is almost no change in the temperature of phase transition between monoclinic phase and tetragonal phase as in the case of a conventional zirconia starting material, resulting in a large difference in thermal expansion coefficient compared to the solid electrolyte. On the other hand, if yttria is added at an amount larger than 7 mol %, the amount of penetration into the space between zirconia crystals becomes too large resulting in an excessive rise of the phase transition temperature, which brings about a similar, large difference in thermal expansion coefficient from the solid electrolyte also in this case. Therefore, the most preferable addition amount of yttria is 5–7 mol %.

When the obtained oxygen concentration detecting device 1 was subjected to cold-hot durability tests, good results without any exfoliation of the protecting layer were obtained.

By varying the composition of the protecting layer 19 used in the oxygen concentration detecting device of the invention, the obtained oxygen concentration detecting devices were subjected to cold-hot durability evaluations.

The results are shown in Tables 1 and 2.

Herein, the specific surface area of the zirconia, which is a main starting material of the protecting layer 19, was measured using a Flowsorb Type 230 (manufactured by Shimazu Co.) by BET method. Namely, the area was calculated on the basis of the quantity of monomolecular nitrogen absorbed on the surface of zirconia particles.

The particle size was measured using a Microtrack manufactured by Nikkiso Co.).

The void ratio of the sintered partially stabilized zirconia was measured by mercury injection method.

The crystal composition was calculated from the integral intensity of R-ray diffraction peaks according to $M/C = [I_{M(111)} + I_{M(\bar{1}11)}]/[I_{M(111)} + I_{M(\bar{1}11)} + I_{C(111)}]$, wherein M:monoclinic phase, C:cubic phase and I:integral intensity.

The cold-hot durability tests were carried out under the condition of environmental change of 1000° C.×12 minutes (in combustion gas) and 200° C.×8 minutes (left in atmosphere) as one cycle of 20 minutes.

Those results without any exfoliation even after 1000 cycles were judged to be preferable.

TABLE 1

| Sample No. | Starting Material Characteristics | | Sintered Material Characteristics | | Result of Cold-Hot Durability Test |
|---|---|---|---|---|---|
| | Specific Surface area m²/g | Particle Size μm | Crystal Composition (M/C) % | void Ratio % | |
| 1 | 3.0 | 0.84 | 20 | 28 | good |
| 2 | 3.5 | 1.10 | 19 | 21 | " |
| 3 | 4.1 | 0.93 | 20 | 20 | " |
| 4 | 4.5 | 0.80 | 18 | 18 | " |
| 5 | 4.5 | 1.01 | 19 | 20 | " |
| 6 | 5.0 | 0.82 | 19 | 18 | " |
| 7 | 5.5 | 0.84 | 18 | 18 | " |
| 8 | 3.7 | 0.85 | 21 | 20 | " |
| 9 | 4.6 | 1.50 | 17 | 26 | " |
| 10 | 3.9 | 1.08 | 19 | 21 | " |
| 11 | 4.6 | 1.05 | 21 | 22 | " |
| 12 | 6.4 | 0.96 | 22 | 19 | broken at 1000th cycle |
| 13 | 6.4 | 1.40 | 18 | 25 | broken at 1000th cycle |

TABLE 2

| Sample No. | Starting Material Characteristics | | Sintered Material Characteristics | | Result of Cold-Hot Durability Test |
|---|---|---|---|---|---|
| | Specific Surface area m²/g | Particle Size μm | Crystal Composition (M/C) % | void Ratio % | |
| 14 | 7.0 | 4.00 | 20 | 45 | exfoliated at 300th cycle |
| 15 | 9.9 | 0.98 | 17 | 17 | exfoliated at 300th cycle |
| 16 | 8.6 | 1.30 | 19 | 25 | exfoliated at 300th cycle |

As Tables 1 and 2 clearly show, when the specific surface area of zirconia was not less than 7 m²/g (Samples No. 14, 15 and 16), cracks were developed in any case, and exfoliation of the protecting layer occurred.

In contrast to this, when the specific surface area of zirconia was 6.4 m²/g (Samples No. 12 and 13), neither breakage nor exfoliation of the protecting layer occurred up to 1000th cycle. Particularly, when the specific surface area was not larger than 6 m²/g (Samples No. 1–11), no breakage or the like of the protecting layer occurred even after 3000th cycle, and it was found that an oxygen concentration detecting device having an extremely good protecting layer could be obtained.

When the specific surface area of zirconia was smaller than 3.0 m²/g, its sintering property decreased remarkably, so that it was extremely difficult to form a protecting layer 19.

FIG. 3 shows the thermal expansion cooling curves of the protecting layer against temperature obtained by varying the specific surface area of each zirconia.

In FIG. 3, A indicates the case where the specific surface area is 7 m²/g, B indicates the case where the specific surface area is 5.5 m²/g, C indicates the case where the specific surface area is 4.1 m²/g and D indicates the case where the specific surface area is 3.0 m²/g.

As FIG. 3 clearly shows, as the specific surface area of zirconia becomes smaller, the temperature of phase transition between monoclinic phase and tetragonal phase becomes higher, so that the amount of transition in the temperature region of from 500° to 1000° C. is reduced and hysteresis due to the volume change during heating up and cooling down is also reduced.

In the above example, the protecting layer 19 obtained by the present invention was applied to an oxygen concentration detecting device having a wedge shape detecting part 3. However, the present invention is not limited to a wedge shape nor to any particular shape and it may be applied to for example, a detecting part of a cylindrical shape or that of a rectangular pillar shape.

Moreover, in the above example, application was made to a stacked type oxygen concentration detecting device, but, application can also be made to a cup type oxygen concentration detecting device having no supporting body.

Furthermore, in the above example, the insulating layer 19 of the present invention was used as a protecting layer of the oxygen concentration cell type oxygen concentration detecting device, but, it can also be applied to the diffusion layer of a limiting current type oxygen concentration detecting device.

Also, in the above example, yttria was used as a divalent or trivalent metal oxide, but, the metal oxide is not limited to yttria; magnesia or calcia may also be used.

What is claimed is:

1. An oxygen concentration detecting device comprising:

a solid electrolyte made of a partially stabilized zirconia, one face of said solid electrolyte being adapted to be exposed to a gas to be measured;

a measuring electrode formed on said face of said solid electrolyte and adapted for exposure to said gas;

a second electrode formed on an opposite face of said solid electrolyte and together with said measuring electrode forming a pair of electrodes sandwiching said solid electrolyte; and an insulating layer which is a porous partially stabilized sintered body and which covers said measuring electrode, said porous partially stabilized sintered body consisting essentially of zirconia and a 5–7 mol % yttria metal oxide, said zirconia having a specific surface area of not less than 3 m²/g and not more than 6.4 m²/g before sintering, and said 5–7 mol % yttria metal oxide being penetrated into spaces between crystals of said zirconia to elevate a temperature of phase transition between monoclinic phase and tetragonal phase of said zirconia sufficiently to cause said insulating layer to have approximately the same thermal expansion coefficient as said solid electrolyte.

2. An oxygen concentration detecting device as claimed in claim 1, wherein said 5–7 mol % yttria metal oxide is one selected from the group consisting of a divalent metal oxide and a trivalent metal oxide.

3. An oxygen concentration detecting device as claimed in claim 1, wherein said thermal expansion coefficient is $7-9\times 10^{-6}/°C$. at 1000° C.

4. An oxygen concentration detecting device as claimed in claim 1, wherein said specific surface area is not less than 3 $m^2/g$ and not more than 6 $m^2/g$.

5. An oxygen concentration detecting device comprising:

a solid electrolyte made of a partially stabilized zirconia, one face of said electrolyte being adapted to be exposed to a gas to be measured;

a measuring electrode formed on said face of said solid electrolyte for exposure to said gas;

a second electrode formed on an opposite face of said solid electrolyte and together with said measuring electrode forming a pair of electrodes sandwiching said solid electrolyte; and an insulating layer which is a porous partially stabilized sintered body and which covers said measuring electrode, said porous partially stabilized sintered body being made of zirconia and yttria, said zirconia having a specific surface area of not less than 3 $m^2/g$ and not more than 6.4 $m^2/g$ before sintering, and an amount of said yttria being 5–7 mol %.

6. A method for producing an oxygen concentration detecting device comprising the steps of:

forming a measuring electrode on one face of a solid electrolyte in such a manner that it is adapted to be exposed to a gas to be measured, said solid electrolyte being made of a partially stabilized zirconia;

forming a second electrode on an opposite face of said solid electrolyte;

forming zirconia and a 5–7 mol % yttria metal oxide on said measuring electrode, said zirconia having a specific surface area of not less than 3 $m^2/g$ and not more than 6.4 $m^2/g$; and sintering said solid electrolyte, said measuring electrode, said second electrode, said zirconia and said 5–7 mol % yttria metal oxide so that an insulating layer made of a porous partially stabilized material is formed, said insulating layer consisting essentially of said zirconia and said 5–7 mol % yttria metal oxide, and said 5–7 mol % yttria metal oxide being penetrated into spaces between crystals of said zirconia to elevate a temperature of phase transition between monoclinic phase and tetragonal phase of said zirconia sufficiently to cause said solid electrolyte and said insulating layer to have approximately the same thermal expansion coefficient.

7. A method for producing an oxygen concentration detecting device as claimed in claim 6, wherein said sintering step is a step of simultaneously sintering said solid electrolyte, said measuring electrode, said second electrode, said zirconia and said 5–7 mol % yttria metal oxide.

8. A method for producing an oxygen concentration detecting device as claimed in claim 7, wherein said 5–7 mol % yttria metal oxide is one selected from the group consisting of a divalent metal oxide and a trivalent metal oxide.

9. A method for producing an oxygen concentration detecting device as claimed in claim 7, wherein said thermal expansion coefficient is $7-9\times 10^{-6}/°C$. at 1000° C. after said sintering step.

10. A method for producing an oxygen concentration detecting device as claimed in claim 6, wherein said specific surface area is not less than 3 $m^2/g$ and not more than 6 $m^2/g$.

11. A method for producing an oxygen concentration detecting device as claimed in claim 6, wherein said specific surface area is measured by BET method in said step of forming zirconia and said 5–7 mol % yttria metal oxide.

12. A method for producing an oxygen concentration detecting device comprising the steps of:

forming a measuring electrode on one face of a solid electrolyte in such a manner that it is adapted to be exposed to a gas to be measured, said solid electrolyte being made of a partially stabilized zirconia;

forming a second electrode on an opposite face of said solid electrolyte;

forming zirconia and yttria on said measuring electrode, said zirconia having a specific surface area of not less than 3 $m^2/g$ and not more than 6.4 $m^2/g$, and an amount of said yttria being 5–7 mol %; and sintering said solid electrolyte, said measuring electrode, said second electrode, said zirconia and said yttria so that an insulating layer made of a porous partially stabilized material is formed on said measuring electrode, said insulating layer including said zirconia and said yttria.

13. A method for producing an oxygen concentration detecting device as claimed in claim 12, wherein said specific surface area is measured by BET method in said step of forming zirconia and yttria.

* * * * *